United States Patent [19]

Fogarty et al.

[11] Patent Number: 4,762,130
[45] Date of Patent: Aug. 9, 1988

[54] CATHETER WITH CORKSCREW-LIKE BALLOON

[75] Inventors: Thomas J. Fogarty, 770 Welch Rd., Palo Alto, Calif. 94304; Thomas B. Kinney, San Diego; James C. Finn, III, Menlo Park, both of Calif.

[73] Assignee: Thomas J. Fogarty, Palo Alto, Calif.

[21] Appl. No.: 3,589

[22] Filed: Jan. 15, 1987

[51] Int. Cl.⁴ ............................................. A61M 25/00
[52] U.S. Cl. ................... 128/348.1; 128/344; 128/356; 604/96
[58] Field of Search ................. 604/96–103; 128/268, 10, 344, 348.1, 304, 356

[56] References Cited

U.S. PATENT DOCUMENTS

| 1,245,325 | 11/1917 | Dunn | 604/96 |
| 3,438,375 | 4/1969 | Ericson | 604/268 X |
| 4,030,503 | 6/1977 | Clark | 128/304 |
| 4,515,587 | 5/1985 | Schiff | 128/344 X |
| 4,573,966 | 3/1986 | Weikl et al. | 604/101 X |
| 4,681,564 | 7/1987 | Landreneau | 604/96 X |
| 4,706,671 | 11/1987 | Weinrib | 128/348.1 |

FOREIGN PATENT DOCUMENTS 584856 12/1977 U.S.S.R. ............... 128/348.1

Primary Examiner—Dalton L. Truluck
Attorney, Agent, or Firm—Limbach, Limbach & Sutton

[57] ABSTRACT

A helical balloon is attached to the distal end of a catheter to serve when inflated as a therapeutic tool for the removal of blood clots and as a diagnostic tool for physical measurements and the application of treatment and other materials.

12 Claims, 4 Drawing Sheets

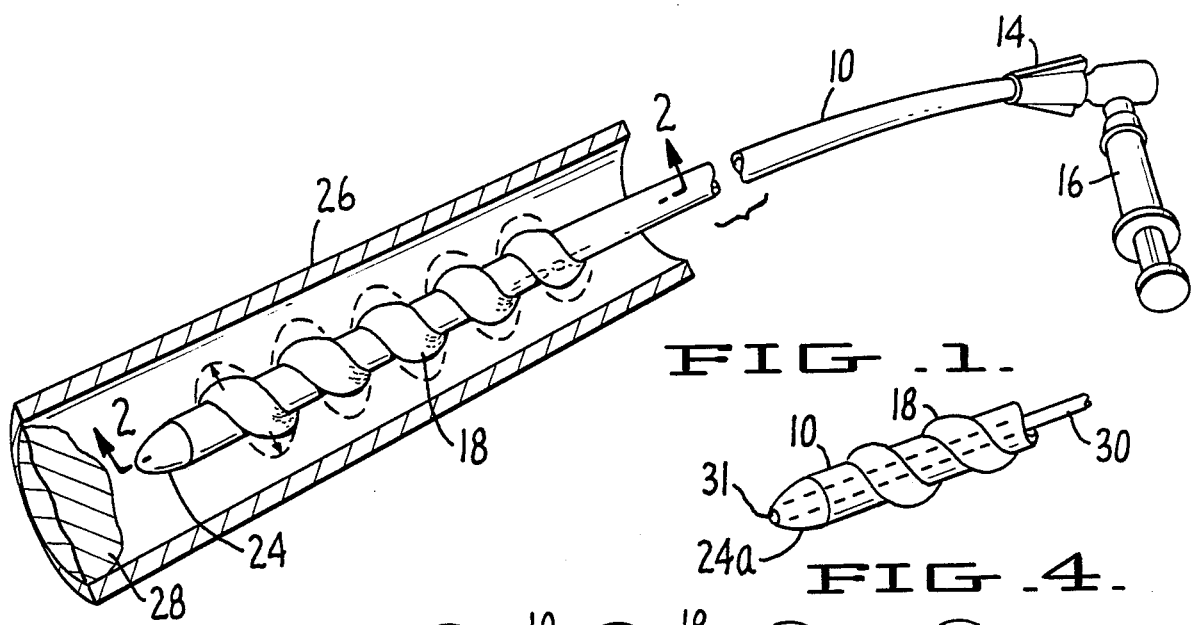
FIG. 1.
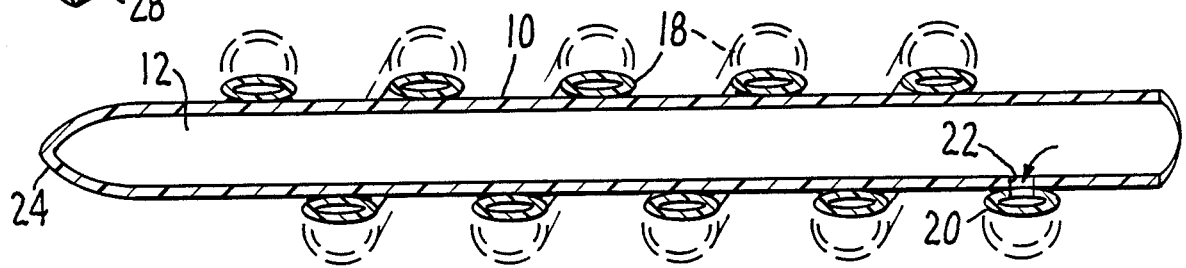
FIG. 2.
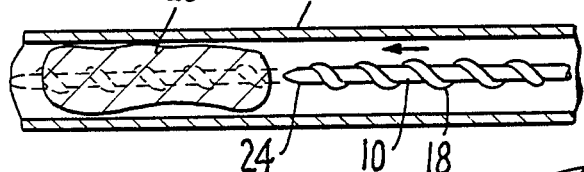
FIG. 3A.
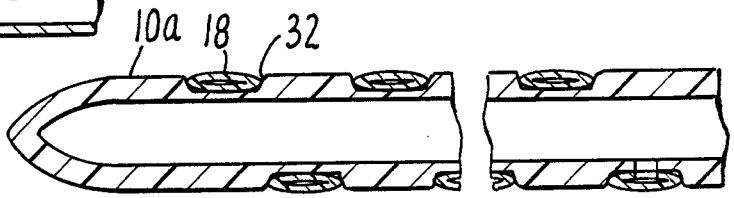
FIG. 4.
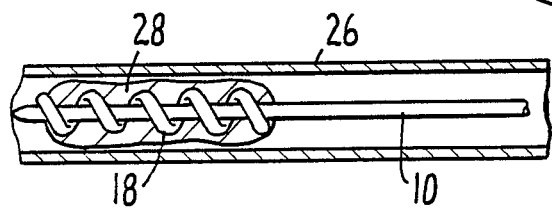
FIG. 3B.
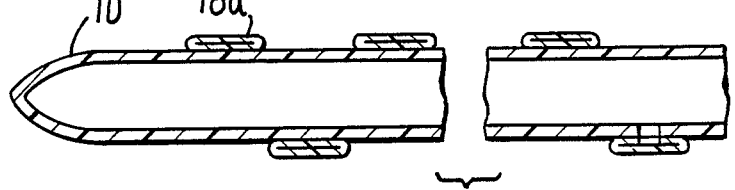
FIG. 5.
FIG. 3C.
FIG. 6.

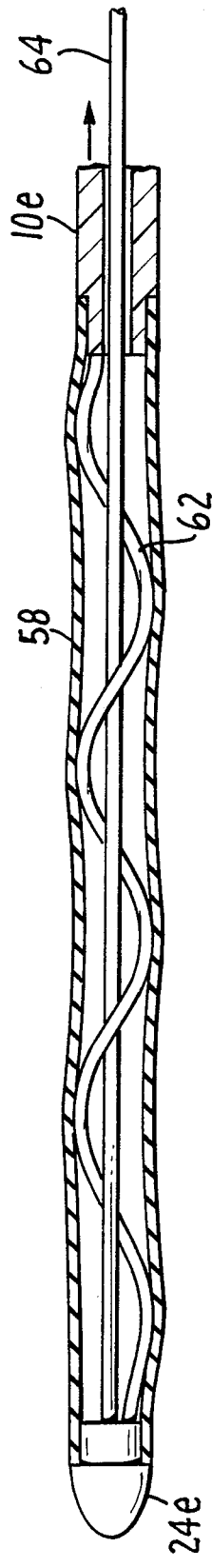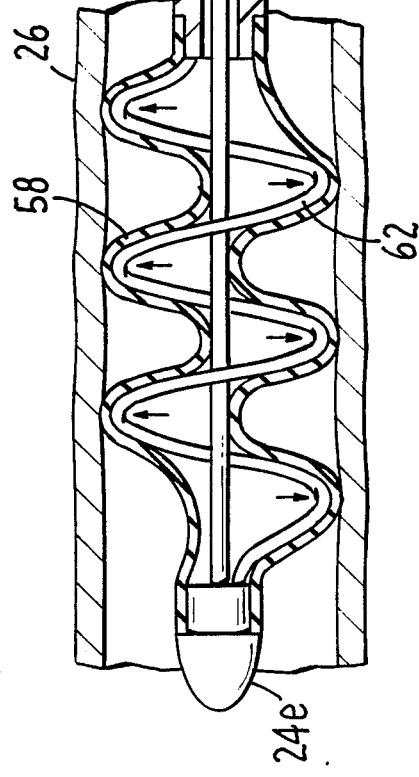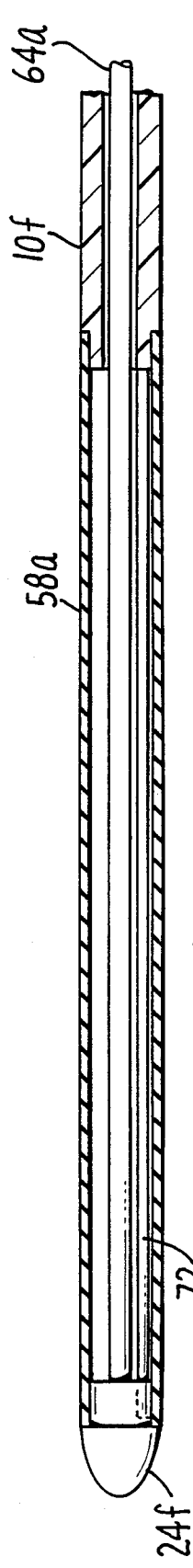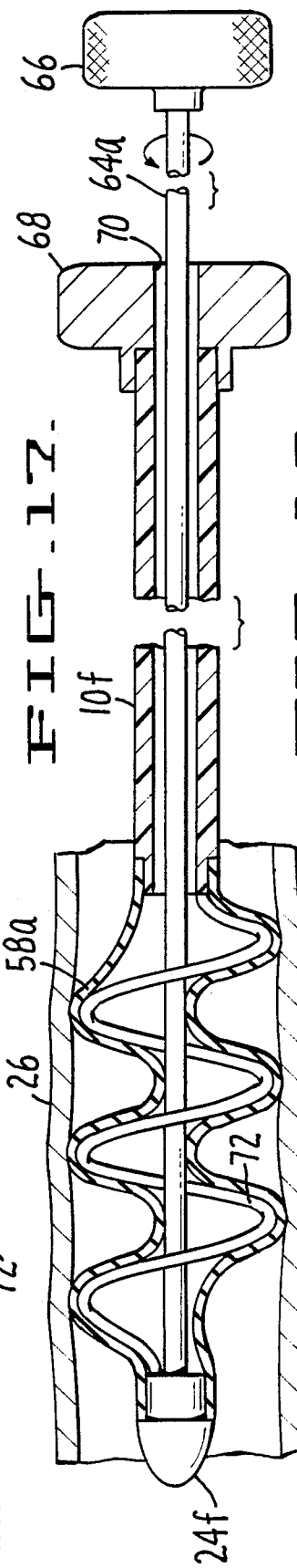

CATHETER WITH CORKSCREW-LIKE BALLOON

BACKGROUND OF THE INVENTION

The present invention relates to catheters and, more particularly, to improved catheters for use as embolectomy catheters and flow-directed diagnostic catheters. In its more specific aspects, the invention is directed to such catheters which employ balloons which may be expanded into a helical configuration.

It is well-known in the art to provide embolectomy catheters with annular balloon means for blood clot removal. U.S. Pat. No. 3,435,826 to Thomas J. Fogarty, one of the coinventors herein, discloses such a catheter.

It is also known in the art to provide embolectomy catheters with a wire or blade in the shape of a spiral helix. Such catheters are rotated to screw the helix into the clot, following which the catheter is removed from the blood vessel without rotation. A catheter of this type is shown in U.S. Pat. No. 4,030,503 to Clark.

Embolectomy catheters have also been provided with annular balloons having flexible protrusions adapted to bite into the clot upon inflation of the balloons to enable the clot to be pulled free by withdrawal of the catheter. Such a catheter is shown in U.S. Pat. No. 3,635,223 to Klieman.

Catheters have also been provided with successively inflatable helical balloon sections to render the catheters self-propelling. A catheter of this type is shown in U.S. Pat. No. 3,485,237 to Bedford.

SUMMARY OF THE INVENTION

The subject catheter comprises a catheter body or tube with a balloon either extending around and secured proximal the distal end of the tube, or secured to and extending from the distal end of the tube. In certain embodiments, the balloon is attenuated and disposed around the tube, with a port within the tube disposed in fluid communication with the interior of the balloon. In other embodiments, the balloon comprises a self-retracting sleeve concentrically received on the tube, with a port within the tube in fluid communication with the interior of the sleeve. Other embodiments employ a balloon containing a wire which may be expanded into a helical configuration to conform the balloon to such a configuration.

When used as an embolectomy catheter, the distal end of the catheter is pushed through a blood clot to be removed with the balloon in a deflated or contracted condition. Thereafter, the balloon is expanded into the helical configuration so that it grips or engages the clot. The concept here is to apply an expansionary balloon force to the interior wall of the blood vessel along a helical path such as to avoid the application of diametrically opposed forces, with possible perforation or abrasion effect on the vessel wall.

By providing one or both ends of the helical balloon with sealing loops, the flow of blood within the vessel may be utilized to propel the catheter along the vessel.

By providing the catheter with a plurality of lumens, a through lumen and one or more side opening lumens, the subject catheter is adapted for use for diagnostic purposes, such as pressure measurements, withdrawal of samples, the injection of medicants, etc.

A principal object of the invention is to provide an embolectomy catheter with a balloon which reduces abrasion to the wall of the vessel within which the catheter is used.

Another object of the invention is to provide such an embolectomy catheter wherein the balloon is of a helical configuration so as to increase the pulling surface area of engagement between the clot being removed and the balloon.

Another object of the invention is to provide such an embolectomy catheter which will not pinch off and separate the clot being removed.

Another object of the invention is to provide an inflatable balloon diagnostic catheter which may be placed by inflating the balloon and then permitting blood flow to move the catheter.

Yet another object is to provide such a diagnostic catheter with multiple lumens to measure pressure.

Still another object of the invention is to provide such a diagnostic catheter wherein arterial contact is minimized during flow placement and wherein, once placed, the pressure points provided by the balloon are not directly opposite one another.

The foregoing and other objects will become more apparent when viewed in light of the accompanying drawings and following detailed description.

BRIEF DESCRIPTION OF THE DRAWINGS

FIG. 1 is a view in perspective of a first embodiment of the embolectomy catheter in extending relation along a blood vessel;

FIG. 2 is an enlarged cross-sectional view taken on the plane designated by line 2—2 of FIG. 1;

FIGS. 3A, 3B, and 3C illustrate the manner of use of the first embodiment of the catheter in the removal of a blood clot;

FIG. 4 is a partial view of a modified form of the first embodiment embolectomy catheter wherein an interior through lumen catheter is provided;

FIG. 5 is a view like FIG. 2 illustrating a variant of the first embodiment catheter wherein the external surface of the catheter is grooved to receive the helical balloon;

FIG. 6 is a view like FIG. 2, showing another variant of the first embodiment catheter which, in this case, is provided with an attenuated balloon which collapses to a very flat profile;

FIG. 15 is a cross-sectional elevational view of a fourth embodiment of the subject embolectomy catheter, with the balloon of the catheter in the contracted condition;

FIG. 16 is a cross-sectional elevational view of the fourth embodiment embolectomy catheter, with the catheter shown received within a blood vessel and the balloon in an expanded condition;

FIG. 17 is a cross-sectional elevational view of a fifth embodiment of the subject embolectomy catheter, with the balloon shown in a contracted condition; and FIG. 18 is a cross-sectional elevational view of the fifth embodiment embolectomy catheter received within a blood vessel, with the balloon of the catheter in an expanded condition.

DESCRIPTION OF THE FIRST EMBODIMENT EMBOLECTOMY CATHETER

Figure 7:
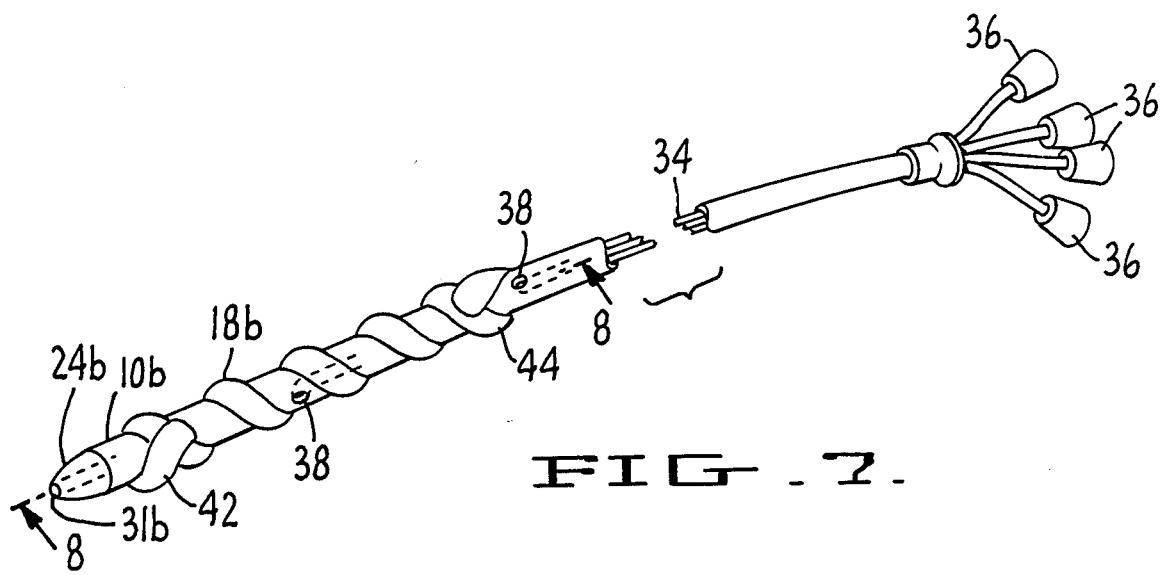
FIG. 7 is a view in perspective of a flow-directed diagnostic catheter embodying the invention.

As shown in FIGS. 1, 2 and 3, this embodiment comprises an elongate flexible catheter or tube 10 having a lumen 12, syringe hub 14, syringe 16 and elastomeric balloon 18. The balloon 18 is wrapped around the distal end of the tube 10 under tension in the pattern of an attenuated helix. At least the end portions of the balloon are bounded to the tube 10. The entire length of the balloon may be bounded to the tube, if desired. The proximal end of the balloon (see FIG. 2) and the adjacent wall of the tube 10 are provided with aligned ports 20 and 22 to establish sealed fluid communication between the interior of the balloon and the lumen 12. Thus, the balloon may be inflated with the syringe 16 through the lumen. The distal end of the tube 10 is closed by a tapered or rounded end portion 24.

FIGS. 1 and 3 show the catheter within a blood vessel 26 containing a fixed clot 28. In use, the catheter is first pushed into and through the clot, as shown in FIG. 3A, with the balloon 18 in a deflated contracted condition. The balloon is then inflated to grip the clot along a helical path, as shown in FIG. 3B. The catheter is then withdrawn, and with it the clot, as shown in FIG. 3C.

The variant of FIG. 4 is identical to the embodiment of FIGS. 1 to 3, except that it is provided with an interior through lumen and the tip is modified to accommodate this lumen. The through lumen is provided by a tubular element or catheter 30. The rounded end or tip portion of this variant is designated by the numeral 24a and is provided with an aperture 31 extending therethrough in sealed fluid communication with the catheter 30. The through lumen provided by the catheter 30 may be employed for a variety of purposes when the catheter is in place, as in FIG. 3B, e.g. to take measurements or to deliver medicants downstream of the clot. Since the lumen of the catheter 10 is sealed from fluid communication with the aperture 31, that lumen may still be used for purposes of inflating the balloon 18.

The variant of FIG. 5 differs from that of FIGS. 1 to 3 only in that the catheter, designated 10a, is provided with a helical recess 32 in which the balloon element 18 is received. This serves to augment the attachment of the balloon to the tube, and also serves to minimize the overall diameter of the catheter in profile.

The variant of FIG. 6 differs from that of FIGS. 1 to 3 only in that the balloon, designated 18a, has a flattened profile when in the deflated condition. This serves, in the absence of the recess 32, to minimize the composite diameter of the catheter when the balloon is in the deflated condition.

DESCRIPTION OF THE FLOW-DIRECTED DIAGNOSTIC CATHETER EMBODIMENT

Figure 8:
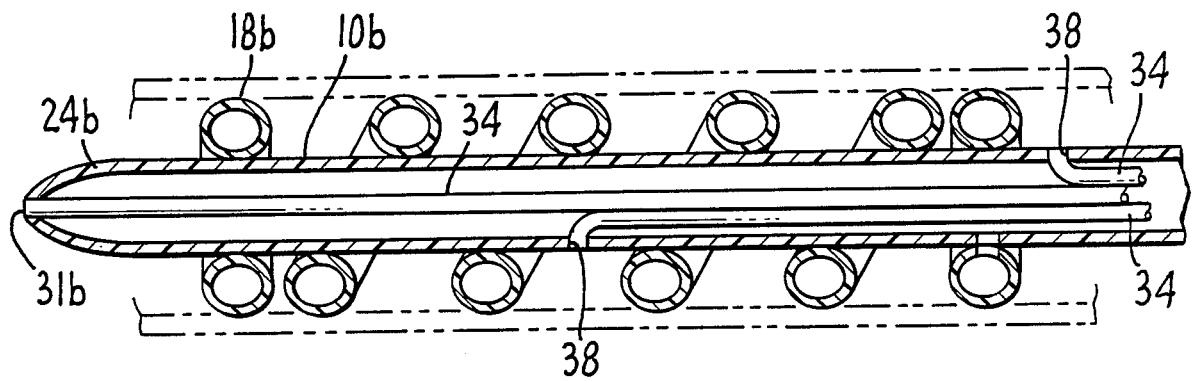
FIG. 8 is an enlarged cross-sectional view of the FIG. 7 catheter, taken on the plane designated by line 8—8, with phantom lines representing a vessel within which the catheter is received and the balloon shown in an inflated condition.

In this embodiment, as shown in FIGS. 7 and 8, the flexible catheter is designated by the numeral 10b and the elastomeric balloon is designated by the numeral 18b. The rounded tip or end portion corresponds to that of the variant shown in FIG. 4 and is designated by the numeral 24b. A bundle of tubular elements 34 extends through the catheter 10b from connectors 36 for syringes or electrical leads. The elements 34 extend either to side openings 38 in the tube 10 or an aperture 31b in the end portion 24b. The elements are secured in sealed communication to the openings 38 and aperture 24b. Thus, the interior lumen of the catheter 10b serves as a conduit to inflate the tube 18b, in a manner similar to that of the first embodiment embolectomy catheter. The distal and proximal ends of the balloon 18b are provided with transverse wrap-around sealing loops 42 and 44.

Although the embodiment of FIGS. 7 and 8 is shown as having two sealing loops 42 and 44, it is sufficient to provide a single sealing loop, either at the distal or proximal end of the balloon 18. In use, when the balloon is inflated, the sealing loop or loops function in the manner of a piston ring to close off blood flow. The blood acting against the sealing loop and tends to self-propel the catheter along the vessel to the site where it is to be used.

The embodiment of FIGS. 7 and 8 is particularly adapted for diagnostic usage. The through and side opening lumens are employed for pressure and temperature measurements, withdrawal of blood samples, injection of medicants, etc. Although this embodiment is primarily designed for diagnostic purposes, it is also possible that it could be used for embolectomy purposes, in the same manner depicted in FIGS. 3A to 3C of the first embodiment embolectomy catheter.

DESCRIPTION OF THE SECOND EMBODIMENT EMBOLECTOMY CATHETER

Figure 9:
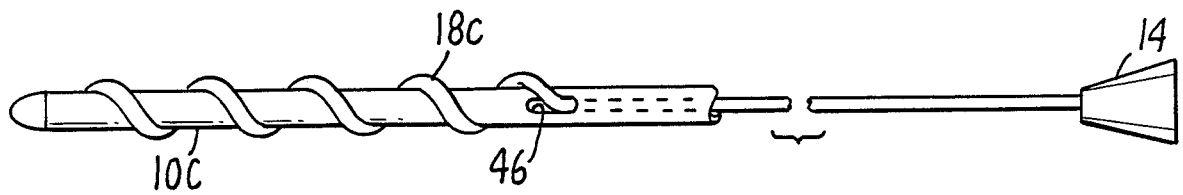
FIG. 9 is a view in elevation of a second embodiment of the subject embolectomy catheter wherein the attenuated balloon element may be selectively extended in length.
Figure 10:
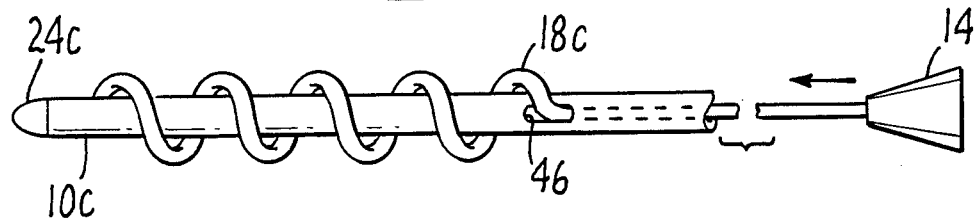
FIG. 10 is a view in elevation of the catheter of FIG. 9, showing the helical balloon in a radially extended condition.

In this embodiment, as shown in FIGS. 9 and 10, the flexible catheter is designated by the numeral 10c and is shown as having a closed rounded distal end portion 24c and a slot-shaped opening 46 through which an elastomeric balloon, designated 18c, extends. Only the extreme distal end of the balloon 18c is fixedly attached to the catheter 10c. This end is sealed, similarly to the first embodiment embolectomy catheter. The proximal end of the balloon 18c extends slidably through the opening 46c and through the lumen of the catheter 10c to syringe hub 14. Movement of the syringe hub toward the helix portion of the balloon serves to feed the balloon outwardly through the opening 46 and cause an increase in the diameter of the helix portion of the balloon, as well as to move the turns of the helix closer together. This enables the balloon to take on an enlarged diameter as compared to a fixed length balloon of the type shown in the embodiment of FIGS. 1 to 3.

In use, the second embodiment of FIGS. 9 and 10 would be adjusted prior to inflation of the balloon to provide the desired radial expansion of the balloon 18c. Then the catheter would be used in essentially the same manner as described with respect to FIGS. 3a to 3c of the first embodiment embolectomy catheter. With the embodiment of FIGS. 9 and 10, it is also possible to retract the balloon to minimize the cross-sectional profile of the catheter assembly during placement.

DESCRIPTION OF THE THIRD EMBODIMENT EMBOLECTOMY CATHETER

Figure 11:
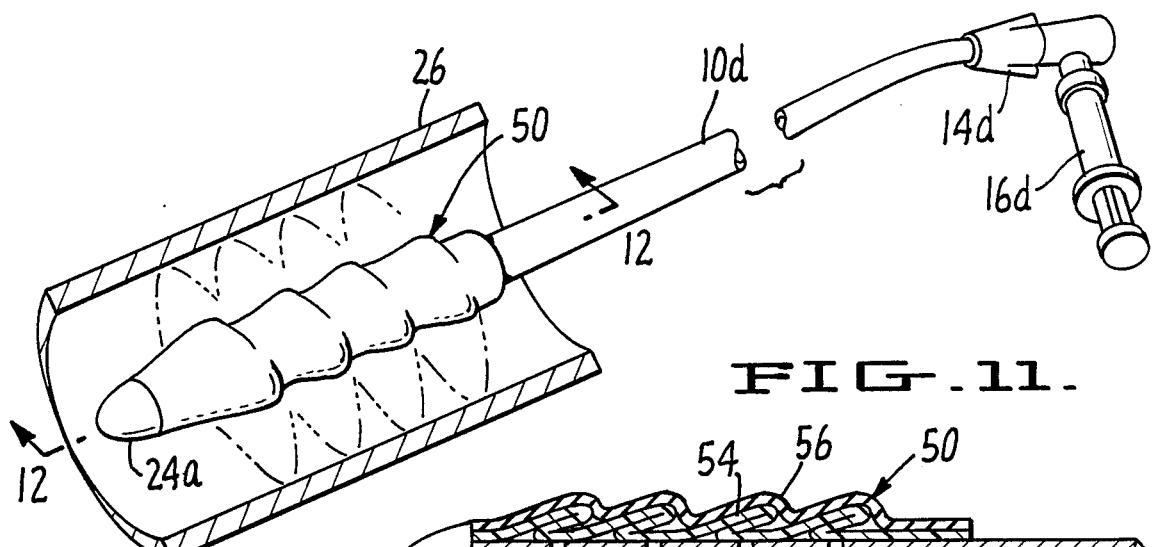
FIG. 11 is a view in perspective of a third embodiment of the subject embolectomy catheter in extending relationship along a blood vessel.
Figure 12:
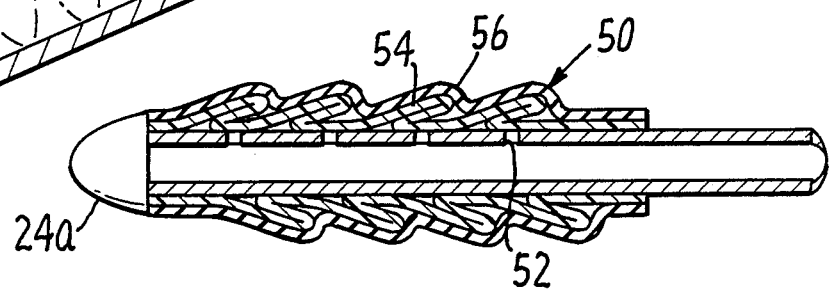
FIG. 12 is an enlarged cross-sectional view taken on the plane designated by line 12—12 of FIG. 11.
Figure 13:
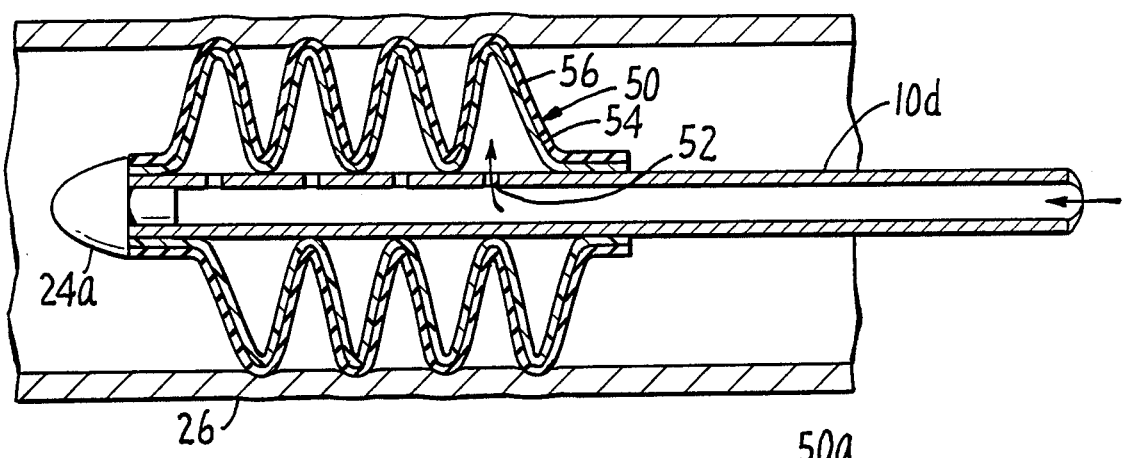
FIG. 13 is a cross-sectional view of the embolectomy catheter of FIG. 11, with the catheter shown in a vessel and the balloon of the catheter inflated into an expanded helical configuration contacting the interior walls of the vessel.

This embodiment, as shown in FIGS. 11 to 13, differs significantly from the prior embodiments in that the balloon element takes the form of a sleeve 50, rather than an elongate attenuated balloon wrapped around the catheter. The sleeve is sealingly secured at its proximal and distal ends to a flexible catheter 10d. Ports 52 establish sealed fluid communication between the interior of the sleeve and the through lumen of the catheter. A rounded end or tip portion 24d closes the distal end of the catheter 10d.

In the preferred embodiment of FIGS. 11 to 13, the sleeve 50 comprises an inner layer 54 of flexible nonelastomeric material and an outer layer 56 of an elastomeric material. The inner layer is conformed to assume a helical configuration upon inflation. The outer layer resiliently stretches to conform to this configuration upon inflation of the balloon and, upon deflation of the balloon, collapses the balloon to the retracted condition shown in FIG. 12.

The catheter 10d has a syringe hub 14d at its proximal end and a syringe 16d connected to this hub. The syringe, similarly to the embodiment of FIGS. 1 to 3, is used to inject fluid into the lumen of the catheter 10d to inflate the balloon 50.

The blood vessel shown in FIGS. 11 and 13 is designated by the numeral 26. In use, the vessel is treated by a procedure corresponding to that shown in FIGS. 3a to 3c. During placement of the catheter assembly, the balloon is in the deflated condition shown in FIGS. 11 and 12 and is passed through the clot to be removed. Once within or past the clot, the balloon 56 is inflated through means of the syringe 16d and then the catheter assembly is removed, taking the clot along with it.

Figure 14:
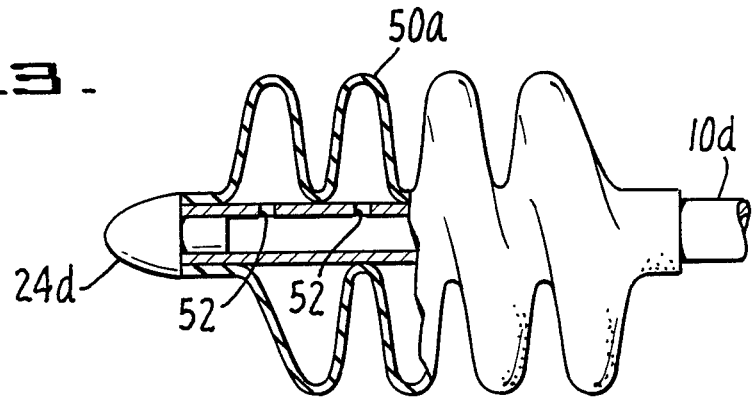
FIG. 14 is an elevational view of a variant of the third embodiment embolectomy catheter, with parts thereof broken away and shown in section.

The variant of FIG. 14 differs from that of FIGS. 11 to 13 only in that the sleeve or balloon element is fabricated of a single layer of elastomeric material. In other words, it does not have a nonelastic inner layer, such as the layer 54. The element 50a is molded to have a predetermined set so that it inflates to a helical configuration, while collapsing to a contracted configuration similar to that shown in FIG. 12 upon deflation. As compared to the embodiment of FIGS. 11 to 13, the variant of FIG. 14 has the advantage that the balloon or sleeve element is of somewhat simplified construction. It does not, however, have the built-in inflation limitation which is provided by having a nonelastomeric inner layer, such as the layer 54. The use of a nonelastomeric layer, such as the layer 54, has the advantage that it limits inflation to a predetermined size and configuration.

DESCRIPTION OF THE FOURTH EMBODIMENT EMBOLECTOMY CATHETER

This catheter, as shown in FIGS. 15 and 16, differs from the previously described embodiments in that the balloon element 58 is not preconfigured into a spiral shape. Rather, it comprises an elongate cylindrical elastomeric sleeve secured to the distal end of a catheter 10e. The distal end of the balloon element 58 is sealed by a rounded end or tip portion 24e. A helical spring wire 62 extends through the element 58 and is engaged at one end with the distal end of the catheter 10e and at the other end with the end or tip portion 24e. A central core or rod element 64 extends slidably through the lumen of the catheter 10e into secure engagement with the balloon through the end or tip portion 24e. This rod provides means whereby the tip 24e may be held in place while the catheter 10e is drawn away from the tip to elongate the balloon element 58.

FIG. 16 shows the fourth embodiment catheter in the expanded balloon condition which it normally assumes under influence of the spring wire 62. In this condition, the wire functions to expand the balloon into a helical configuration. FIG. 15 shows the balloon element in the contracted condition which it assumes upon withdrawing of the catheter 10e relative to the core or rod element 64. Such retraction functions to extend the balloon element and the spring longitudinally and, in turn, reduce the overall profile diameter of the assembly.

In use, the fourth embodiment catheter is introduced into a vessel in the reduced profile condition shown in FIG. 15. This is achieved by applying linear tension to the catheter with respect to the core or rod 64, thus necking down the preset balloon. Although not illustrated, it should be understood that the central core or rod could be retained in this tensioned condition through means of a locking mechanism at the catheter hub. For example, after passing the catheter assembly into or through the clot to be removed, the catheter 10e is released to permit the spring wire to expand the balloon element 58 into the helical condition shown in FIG. 16. Thus, the clot is securely engaged. The clot may then be removed by withdrawing the assembly from the blood vessel, designated 26 in FIG. 16.

DESCRIPTION OF THE FIFTH EMBODIMENT EMBOLECTOMY CATHETER

As shown in FIGS. 17 and 18, this embodiment is similar to the fourth embodiment in that the balloon element, designated 58a, takes the form of a resilient sleeve secured to the distal end of a catheter 10f. Similarly to the fourth embodiment, the distal end of the sleeve 58a is closed by a rounded end or tip portion 24f and the central cord or rod element 64a is secured to this portion and extends therefrom through the catheter 10f. A knob 66 is fixedly secured to the proximal end of the rod 64a. A knob 68 having an opening 70 there through in alignment with the catheter 10f is fixedly secured to the catheter.

The fifth embodiment differs from the fourth embodiment primarily in that it does not employ a preformed helical spring wire, such as the wire 62. Rather, it employs a flexible spring wire 72 of a generally rectilinear configuration secured at its opposite ends to the tip portion 24f and the distal end portion of the catheter 10f. This spring wire is normally extended and the balloon element 58a is in the contracted condition as shown in FIG. 17. Upon twisting of the rod 64a relative to the catheter 10f, through means of the knobs 66 and 68, the spring wire 72 assumes the helical configuration shown in FIG. 18 and elastically deforms the balloon element 58a into this configuration.

The fifth embodiment catheter is introduced into the vessel to be treated in the reduced profile configuration shown in FIG. 17. When the desired location of the assembly is achieved, twisting of the rod 64 relative to the catheter 10f causes the flexible spring wire 72 to wrap around the rod and assume the helical configuration shown in FIG. 18, thus gripping the clot engaged by the assembly. Once so engaged, the assembly is removed, together with the clot, similarly to what is seen in FIG. 3C.

CONCLUSION

From the foregoing description, it is believed apparent that the present invention enables the attainment of the objects initially set forth herein. In particular, it provides an improved embolectomy catheter wherein a clot may be securely engaged and removed, with a minimum of abrasion to the vessel within which it is used. It also provides an ideal diagnostic catheter which may be flow-directed and provides sealed engagement with the vessel within which it is used, with a minimum of friction and abrasion. It should be understood, however, that the invention is not intended to be limited to the specifics of the described embodiments, but rather is defined by the accompanying claims.

We claim:

1. An intravascular catheter comprising: an elongate flexible tube having a through lumen; an inflatable and deflatable helical balloon attached to and carried by said tube adjacent the distal end of said tube, said balloon comprising a plurality of spaced apart helical turns disposed about said tube, at least one end of said balloon extending transversely around said tube and into attached relation to said balloon to thereby form a closed annular sealing loop which is responsive to blood pressure or blood flow within a blood vessel to move said catheter along said vessel; and a port formed in said tube providing communication between said lumen and said balloon.

2. The catheter of claim 1, further comprising a plurality of tubular elements carried within said tube and defining other lumens, said other lumens comprising lumens extending through the wall of said tube into communication with external spaces defined between helical turns of said balloon and a lumen extending along the axis of said tube and through a tapered tip portion thereof.

3. A catheter according to claim 1 wherein said balloon comprises an elongated tubular element of a helical configuration extending around the flexible tube.

4. An intravascular catheter comprising: an elongate flexible tube having a through lumen; an inflatable and deflatable helical balloon attached to and carried by said tube adjacent the distal end of said tube, said balloon comprising an annular sleeve concentrically received around the flexible tube, said sleeve having proximal and distal ends sealed to the tube and being proportioned to define a helical chamber between the tube and the sleeve upon inflation of the balloon with a plurality of spaced apart helical turns disposed about said tube; and a port formed in said tube providing communication between said lumen and said balloon.

5. A catheter according to claim 4 wherein said sleeve is fabricated of an elastomeric material and configured to collapse and contract against the flexible tube upon deflation of the balloon.

6. A catheter according to claim 4 wherein the sleeve is fabricated of a nonelastic flexible inner sheath contained within an elastomeric outer sheath, said outer sheath being configured to contract and collapse the inner sheath against the flexible tube upon deflation of the balloon.

7. An intravascular catheter comprising: an elongate flexible tube; an inflatable and deflatable helical balloon supported by said tube adjacent the distal end of said tube, the distal end of said balloon being attached to said tube, said balloon comprising a plurality of spaced-apart helical turns disposed about said tube, the proximal end of said balloon extending through an opening in said tube and extending along said tube for connection to balloon inflation means, said proximal end of the balloon being manually feedable in one direction through said tube opening to move the helical turns of said balloon away from said tube and increase the effective diameter of the balloon disposed externally of the tube for inflation while reducing the distances between adjacent turns, and being feedable in the other direction through said tube opening to cause said helical turns to bear against said tube and decrease the effective diameter of the balloon disposed externally of the tube for inflation while increasing the distances between adjacent turns.

8. A catheter comprising: a flexible tube having a through lumen and an open distal end; an elongate balloon extending longitudinally from the distal end of the tube, said balloon being movable between contracted and expanded conditions and having an open proximal end secured to the distal end of the tube; an elongate element extending through the balloon, said element being expandible into a helical configuration in intimate contact with the interior of the balloon; and means to expand the element into the helical configuration in response to movement of the element relative to the tube to stretch the balloon into a helical configuration conforming to that of the element.

9. A catheter according to claim 8 wherein: said element comprises a flexible wire within the tube, said wire having one end secured in engagement with the tube and another end secured in engagement with the balloon in spaced relationship to the distal end of the tube; and said movement of the element relative to the tube functions to force the wire into an expanded helical configuration.

10. A catheter according to claim 9 wherein said wire assumes an elongate helical configuration when the balloon is in the contracted condition and is moved axially relative to the tube to force the wire into an expanded helical configuration.

11. A catheter according to claim 9 wherein said wire assumes an elongate generally straight configuration when the balloon is in the contracted condition and is rotated and moved axially relative to the tube to force the wire into an expanded helical configuration.

12. A method of removing an adherent clot from a blood vessel comprising: attaching an elongate balloon in contracted condition to the distal end of a catheter; passing the distal end of said catheter through said clot so that said balloon is within said clot; expanding said balloon into an expanded helical configuration to grip the clot and at least partially conform it to the helical configuration of the balloon; and withdrawing said catheter, and said clot with it, from said blood vessel.

* * * * *